United States Patent
Abbott et al.

(10) Patent No.: US 11,224,671 B2
(45) Date of Patent: Jan. 18, 2022

(54) RELEASE OF CLO₂ GAS FROM PRODUCE PACKAGING FILM

(71) Applicants: Wisconsin Alumni Research Foundation, Madison, WI (US); Bemis Company, Inc., Neenah, WI (US)

(72) Inventors: Nicholas Abbott, Madison, WI (US); Rishabh Jain, Appleton, WI (US); Kevin Nelson, Neenah, WI (US); David Busche, Neenah, WI (US); David Lynn, Middleton, WI (US)

(73) Assignees: Wisconsin Alumni Research Foundation, Madison, WI (US); Bemis Company, Inc., Neenah, WI (US)

( * ) Notice: Subject to any disclaimer, the term of this patent is extended or adjusted under 35 U.S.C. 154(b) by 4 days.

(21) Appl. No.: 15/753,314

(22) PCT Filed: Aug. 18, 2016

(86) PCT No.: PCT/US2016/047612
§ 371 (c)(1),
(2) Date: Feb. 17, 2018

(87) PCT Pub. No.: WO2017/031351
PCT Pub. Date: Feb. 23, 2017

(65) Prior Publication Data
US 2018/0235246 A1 Aug. 23, 2018

Related U.S. Application Data

(60) Provisional application No. 62/206,464, filed on Aug. 18, 2015.

(51) Int. Cl.
*A61L 2/20* (2006.01)
*B32B 27/18* (2006.01)
(Continued)

(52) U.S. Cl.
CPC ............... *A61L 2/20* (2013.01); *A23B 7/144* (2013.01); *B01J 19/123* (2013.01); *B32B 1/02* (2013.01);
(Continued)

(58) Field of Classification Search
CPC .......... B32B 7/02; B32B 27/18; B32B 27/28; B32B 27/30; B32B 27/304; B32B 27/306;
(Continued)

(56) References Cited

U.S. PATENT DOCUMENTS

| 3,754,079 A | 8/1973 | Callerame |
|---|---|---|
| 4,456,511 A | 6/1984 | Fisher |

(Continued)

FOREIGN PATENT DOCUMENTS

| CN | 1355768 A | 6/2002 |
|---|---|---|
| CN | 101195477 A | 6/2008 |

(Continued)

OTHER PUBLICATIONS

U.S. Appl. No. 62/206,464, filed Aug. 18, 2015, Wisconsin Alumni Research Foundation.
(Continued)

*Primary Examiner* — Subbalakshmi Prakash
(74) *Attorney, Agent, or Firm* — Mueting Raasch Group

(57) ABSTRACT

A multilayer produce packaging film includes a first layer and a chlorine dioxide-producing layer. The chlorine dioxide-producing layer includes a polymer composition and a plurality of chlorite ions. The chlorine dioxide-producing layer is substantially free of an energy-activated catalyst and is substantially free of an acid-releasing compound. However, the film is capable of generating chlorine dioxide when exposed to UV light and moisture.

19 Claims, 2 Drawing Sheets

(51) Int. Cl.

| | |
|---|---|
| *B32B 27/30* | (2006.01) |
| *B32B 27/32* | (2006.01) |
| *B32B 7/12* | (2006.01) |
| *B32B 27/36* | (2006.01) |
| *B32B 27/28* | (2006.01) |
| *B32B 7/02* | (2019.01) |
| *B32B 27/34* | (2006.01) |
| *B32B 15/08* | (2006.01) |
| *B65D 1/00* | (2006.01) |
| *B32B 1/02* | (2006.01) |
| *B32B 15/082* | (2006.01) |
| *B32B 15/085* | (2006.01) |
| *B32B 15/20* | (2006.01) |
| *B32B 27/08* | (2006.01) |
| *B32B 27/20* | (2006.01) |
| *B65D 65/40* | (2006.01) |
| *B65D 81/24* | (2006.01) |
| *A23B 7/144* | (2006.01) |
| *C08L 23/12* | (2006.01) |
| *B01J 19/12* | (2006.01) |
| *C01B 11/02* | (2006.01) |
| *C08K 3/24* | (2006.01) |

(52) U.S. Cl.
CPC ............... *B32B 7/02* (2013.01); *B32B 7/12* (2013.01); *B32B 15/08* (2013.01); *B32B 15/082* (2013.01); *B32B 15/085* (2013.01); *B32B 15/20* (2013.01); *B32B 27/08* (2013.01); *B32B 27/18* (2013.01); *B32B 27/20* (2013.01); *B32B 27/28* (2013.01); *B32B 27/30* (2013.01); *B32B 27/304* (2013.01); *B32B 27/306* (2013.01); *B32B 27/32* (2013.01); *B32B 27/322* (2013.01); *B32B 27/34* (2013.01); *B32B 27/36* (2013.01); *B65D 1/00* (2013.01); *B65D 65/40* (2013.01); *B65D 81/24* (2013.01); *C01B 11/024* (2013.01); *C08K 3/24* (2013.01); *C08L 23/12* (2013.01); *A61L 2202/11* (2013.01); *B01J 2219/0879* (2013.01); *B01J 2219/1203* (2013.01); *B32B 2255/10* (2013.01); *B32B 2255/20* (2013.01); *B32B 2255/205* (2013.01); *B32B 2264/10* (2013.01); *B32B 2307/40* (2013.01); *B32B 2307/50* (2013.01); *B32B 2307/71* (2013.01); *B32B 2307/7242* (2013.01); *B32B 2307/7244* (2013.01); *B32B 2307/7246* (2013.01); *B32B 2307/732* (2013.01); *B32B 2307/748* (2013.01); *B32B 2315/00* (2013.01); *B32B 2323/10* (2013.01); *B32B 2405/00* (2013.01); *B32B 2439/06* (2013.01); *B32B 2439/46* (2013.01); *B32B 2439/70* (2013.01); *B32B 2439/80* (2013.01); *C08L 2203/16* (2013.01)

(58) Field of Classification Search
CPC ....... B32B 27/32; B32B 27/322; B32B 27/34; B32B 27/36; B32B 15/20; B32B 15/085; B32B 15/082; B32B 1/02; B32B 27/20; B32B 27/08; B32B 15/08; B32B 7/12; B32B 2307/50; B32B 2307/71; B32B 2307/7242; B32B 2307/7244; B32B 2307/7246; B32B 2307/732; B32B 2307/748; B32B 2439/06; B32B 2439/46; B32B 2439/70; B32B 2439/80; B32B 2264/10; B32B 2307/40; B32B 2255/10; B32B 2255/20; B32B 2255/205; B65D 81/24; B65D 65/40; B65D 1/00; A61L 2/20; A61L 2202/11; B01J 19/123; B01J 2219/1203; B01J 2315/00; B01J 2323/10; B01J 2405/00; C08K 3/24; C01B 11/024; A23B 7/144; C08L 23/12; C08L 2203/16
See application file for complete search history.

(56) References Cited

U.S. PATENT DOCUMENTS

| | | | |
|---|---|---|---|
| 4,585,482 A | 4/1986 | Tice et al. | |
| 4,874,489 A | 10/1989 | Callerame | |
| 5,360,528 A | 11/1994 | Oh et al. | |
| 5,360,609 A | 11/1994 | Wellinghoff | |
| 5,631,300 A | 5/1997 | Wellinghoff | |
| 5,695,814 A | 12/1997 | Wellinghoff et al. | |
| 5,719,100 A | 2/1998 | Zahradnik | |
| 5,888,528 A | 3/1999 | Wellinghoff et al. | |
| 5,922,776 A | 7/1999 | Wellinghoff et al. | |
| 5,965,264 A | 10/1999 | Barenberg et al. | |
| 5,980,826 A | 11/1999 | Barenberg et al. | |
| 6,231,830 B1 | 5/2001 | Madray | |
| 6,554,887 B1* | 4/2003 | Inglis | A01M 1/14 206/484.1 |
| 6,605,304 B1 | 8/2003 | Wellinghoff et al. | |
| 6,767,509 B1 | 7/2004 | Griesbach et al. | |
| 7,273,567 B1 | 9/2007 | Wellinghoff et al. | |
| 7,449,194 B2 | 11/2008 | Lelah et al. | |
| 7,695,692 B2 | 4/2010 | Sanderson | |
| 8,652,411 B2 | 2/2014 | Taguchi et al. | |
| 2005/0079124 A1 | 4/2005 | Sanderson | |
| 2005/0001063 A1 | 5/2005 | Gray et al. | |
| 2006/0000063 A1 | 1/2006 | Callerame | |
| 2006/0068029 A1 | 3/2006 | Mason | |
| 2006/0178445 A1 | 8/2006 | McIntyre | |
| 2008/0026029 A1 | 1/2008 | Wellinghoff et al. | |
| 2008/0299066 A1 | 12/2008 | Wellinghoff et al. | |
| 2009/0000823 A1 | 1/2009 | Williams | |
| 2009/0220739 A1* | 9/2009 | Chougule | B01D 53/228 428/138 |
| 2012/0164025 A1 | 6/2012 | Stockley, III et al. | |
| 2014/0311094 A1 | 10/2014 | Thompson et al. | |
| 2014/0348702 A1 | 11/2014 | Wofford et al. | |
| 2015/0024211 A1 | 1/2015 | Miratsu et al. | |
| 2017/0157904 A1 | 6/2017 | Abbott et al. | |
| 2018/0243456 A1 | 8/2018 | Abbott et al. | |

FOREIGN PATENT DOCUMENTS

| | | |
|---|---|---|
| CN | 102834350 A | 12/2019 |
| EP | 0 611 162 A1 | 11/1994 |
| EP | 1 198 412 B1 | 12/2008 |
| WO | WO 00/69775 A1 | 11/2000 |
| WO | WO 2010/045280 A2 | 4/2010 |
| WO | WO 2016/069864 A2 | 5/2016 |
| WO | WO 2017/031345 A1 | 2/2017 |
| WO | WO 2017/031349 A1 | 2/2017 |
| ZA | 2001/9124 B | 11/2001 |

OTHER PUBLICATIONS

U.S. Appl. No. 15/753,312, filed Aug. 18, 2016, Abbott et al.
U.S. Appl. No. 15/433,510, filed Feb. 15, 2017, Abbott et al.
PCT/US2016/047603, Aug. 18, 2016, Abbott et al.
PCT/US2016/047608, Aug. 18, 2016, Abbott et al.
International Patent Application No. PCT/US2016/047603, filed Aug. 18, 2016; International Search Report / Written Opinion dated Nov. 3, 2016; 11 pages.
International Patent Application No. PCT/US2016/047603), filed Aug. 18, 2016; International Preliminary Report on Patentability dated Mar. 1, 2018; 7 pages.
International Patent Application No. PCT/US2016/047608, filed Aug. 18, 2016; International Search Report/ Written Opinion dated Nov. 15, 2016; 12 pages.
International Patent Application No. PCT/US2016/047608, filed Aug. 18, 2016; International Preliminary Report on Patentability dated Mar. 1, 2018, 8 pages.

(56) References Cited

OTHER PUBLICATIONS

International Patent Application No. PCT/US2016/047612, filed Aug. 18, 2016; International Search Report / Written Opinion dated Nov. 11, 2016, 12 pages.

International Patent Application No. PCT/US2016/047612, filed Aug. 18, 2016; International Preliminary Report on Patentability dated Mar. 1, 2018, 8 pages.

Aieta et al. "Determination of chlorine dioxide, chlorine, chlorite, and chlorate in water" 1984 *American Water Works Association* pp. 64-70.

Appendini et al. "Review of antimicrobial food packaging" 2002 *Innovative Food Science & Emerging Technologies* vol. (3):pp. 113-126.

Burton et al. "Effect of gaseous chlorine dioxide on indoor microbial contaminants" 2008 *Journal of the Air & Waste Management Association* vol. (58):pp. 647-656.

Buxton et al. Radiation chemistry and photochemistry of oxychlorine ions. Part 1, 2, and 3—1972 *Journal of the Chemical Society, Faraday Transactions 1: Physical Chemistry in Condensed Phases* vol. (68):pp. 947-977.

Cosson et al., "Photodecomposition of Chlorine Dioxide and Sodium Chlorite in Aqueous Solution by Irradiation with Ultraviolet Light" 1994 *Industrial and Engineering Chemistry Research*, vol. (33):pp. 1468-1475.

Diffey "Sources and measurement of ultraviolet radiation" 2002 *Methods* vol. (28):pp. 4-13.

Gagnon et al. "Disinfectant efficacy of chlorite and chlorine dioxide in drinking water biofilms" 2005 *Water Research* vol. (39):pp. 1809-1817.

Gibbs et al. "Gaseous chlorine dioxide as an alternative for bedbug control" 2012 *Infection Control and Hospital Epidemiology* vol. (33):pp. 495-499.

Gómez-López et al. "Chlorine dioxide for minimally processed produce preservation: a review" 2009 *Trends in Food Science &Technology* vol. (20):pp. 17-26.

Gordon et al. "The chemistry of chlorine dioxide" 1972 *Progress in Inorganic Chemistry* vol. (15):pp. 201-286.

Han "Antimicrobial food packaging" 2003 *Novel food packaging techniques* pp. 50-70.

Hirneisen et al. "Viral Inactivation in Foods: A Review of Traditional and Novel Food-Processing Technologies" 2010 *Comprehensive Reviews in Food Science and Food Safety* vol. (9):pp. 3-20.

Jang et al. "Measurement of chlorine dioxide penetration in dairy process pipe biofilms during disinfection" 2006 *Applied Microbiology and Biotechnology* vol. (72):pp. 368-376.

Kaczur et al. "Chlorine oxygen acids and salts, chlorous acid, chlorites, and chlorine dioxide" 2000 *Kirk-Othmer Encyclopedia of Chemical Technology*.

Karpel et al. "Photodecomposition of chlorine dioxide and chlorite by u. v.-irradiation—Part II. Kinetic study" 1992 *Water Research* vol. (26):pp. 1665-1672.

Lee et al. "Efficacy of chlorine dioxide gas as a sanitizer of lettuce leaves" 2004 *Journal of Food Protection®* vol. (67):pp. 1371-1376.

Ruiz, R.P. "Karl Fischer Titration" 2001 *Current Protocols in Food Analytical Chemistry*, pp. A1.2.1-A1.2.4.

Scholz, E. Chapter 3 "Titration Techniques," *Karl Fischer titration: determination of water 1984 Springer-Verlag*, pp. 15-25.

Sy et al. "Evaluation of gaseous chlorine dioxide as a sanitizer for killing *Salmonella*, *Escherichia coli* 0157: H7, Listeria monocytogenes, and yeasts and molds on fresh and fresh-cut produce" 2005 *Journal of Food Protection®* vol. (68):pp. 1176-1187.

Vogt et al. "Chlorine Oxides and Chlorine Oxygen Acids" 2005 *Ullmann's Encyclopedia of Industrial Chemistry*. Wiley-VCH Verlag GmbH & Co.KGaA.

Volk et al. "Implementation of chlorine dioxide disinfection: Effects of the treatment change on drinking water quality in a full-scale distribution system" 2002 *Journal of Environmental Engineering and Science* vol. (1):pp. 323-330.

Weaver-Meyers et al. "Controlling mold on library materials with chlorine dioxide: an eight-year case study" 1998 *The Journal of academic librarianship* vol. (24):pp. 455-458.

Whitney et al. "Inactivation of Bacillus anthracis spores" 2003 *Emerging infectious diseases* vol. (9):p. 623-627.

Wilson et al. "Effect of chlorine dioxide gas on fungi and mycotoxins associated with sick building syndrome" 2005 *Applied and Environmental Microbiology* vol. (71):pp. 5399-5403.

Dehydration, Hawley's Condensed Chemical Dictionary, R.J. Lewis ed., Mar. 15, 2007 (Year: 2007).

* cited by examiner

RELEASE OF CLO₂ GAS FROM PRODUCE PACKAGING FILM

CROSS-REFERENCE TO RELATED APPLICATIONS

This application is the § 371 U.S. National State of International Application No. PCT/US2016/047612, filed Aug. 18, 2016, which claims the benefit of U.S. Provisional Patent Application No. 62/206,464, filed on Aug. 18, 2015, which application is hereby incorporated herein by reference to the extent that it does not conflict with the present disclosure.

FIELD

This disclosure relates generally to the release of a disinfectant gas from packaging film for produce. In particular, the disclosure is directed to compositions and methods for the controlled release of $ClO_2$ gas from packaging for produce.

BACKGROUND

Chlorine dioxide ($ClO_2$) is a powerful oxidizing agent and disinfectant. It is used today primarily in bleaching processes in the paper pulp industry and as a disinfectant for water treatment. It has also been shown to be useful as a broad spectrum biocide in various applications such as food processing, fungus and mold fumigation, biofilm treatment and even in the killing of bedbugs and hardy anthrax spores.

Accordingly, it may be desirable to generate packaging films capable of releasing gaseous $ClO_2$ to inhibit microbial growth on products, such as food products including produce, packaged in the films. However, timing and amount of release of $ClO_2$ gas from packaging films can be difficult to control.

Wellinghoff et al. have devised polymer packaging films which release $ClO_2$ gas when the films come in contact with moisture. See, for example, U.S. Pat. Nos. 5,360,609 and 5,888,528. In the system described in U.S. Pat. No. 5,360,609, a mixture of an acid anhydride and chlorite in different phases (hydrophobic and hydrophilic) can produce $ClO_2$ when the anhydride is hydrolyzed to produce an acid, which reacts with chlorite. Notably, this system produces $ClO_2$ upon contact with moisture from any source, and thus the timing of $ClO_2$ production can be difficult to control.

Wellinghoff et al. have also devised a polymeric composition containing chlorite anion and a photo-activated catalyst that triggers the production of $ClO_2$ upon exposure to light. See, for example, U.S. Patent Publication No. 2008/0299066. However, the timing of $ClO_2$ production in this system is difficult to control because $ClO_2$ is produced whenever the polymer is exposed to light, including inadvertent exposure to ambient visible light.

It would be desirable to provide a packaging for produce that allows for more controlled release of $ClO_2$ gas.

SUMMARY

Described herein, among other things, is a multilayer packaging film for produce that provides for controlled, on-demand release of $ClO_2$ gas to deodorize or disinfect produce packaged in the film. The packaging described herein releases $ClO_2$ gas upon exposure to both ultraviolet (UV) light and moisture.

In various embodiments, a multilayer produce package film is described herein. The multilayer produce packaging film comprises a first layer and a chlorine dioxide-producing layer. The chlorine dioxide-producing layer comprises a polymer composition and a plurality of chlorite ions and is substantially free of an energy-activated catalyst and is substantially-free of an acid-releasing compound. Yet, the films generate chlorine dioxide when exposed to UV light in the presence of moisture.

The packaging described herein provides for more controlled release of $ClO_2$ gas than previously described chlorine dioxide-releasing films, such as those described by Wellinghoff et al. In addition, by requiring the use of UV light, rather than visible light-activated photocatalysts, such as those described by Wellinghoff et al., the produce packaging films described herein do not release significant amounts of chlorine dioxide when exposed to ambient visible light. Accordingly, the films described herein can be manufactured and stored under typical lighting conditions, as opposed to in the dark, as well as manufactured and stored in humid conditions, without premature generation of chlorine dioxide. As such, the ability of the films described herein to release significant or effective amounts of chlorine dioxide at a desired time can be enhanced relative to previously described chlorine-generating films that include one or both of an acid-releasing compound and an energy-activated catalyst, which may be prematurely depleted of chlorite ions.

Additional features and advantages of the subject matter of the present disclosure will be set forth in the detailed description which follows, and in part will be readily apparent to those skilled in the art from that description or recognized by practicing the subject matter of the present disclosure as described herein, including the detailed description which follows, the claims, as well as the appended drawings.

It is to be understood that both the foregoing general description and the following detailed description present embodiments of the subject matter of the present disclosure, and are intended to provide an overview or framework for understanding the nature and character of the subject matter of the present disclosure as it is claimed. The accompanying drawings are included to provide a further understanding of the subject matter of the present disclosure, and are incorporated into and constitute a part of this specification. The drawings illustrate various embodiments of the subject matter of the present disclosure and together with the description serve to explain the principles and operations of the subject matter of the present disclosure. Additionally, the drawings and descriptions are meant to be merely illustrative, and are not intended to limit the scope of the claims in any manner.

BRIEF DESCRIPTION OF THE DRAWINGS

The following detailed description of specific embodiments of the present disclosure can be best understood when read in conjunction with the following drawings, where like structure is indicated with like reference numerals and in which.

The schematic drawings are not necessarily to scale. Like numbers used in the figures refer to like components, steps and the like. However, it will be understood that the use of

Figure 1:
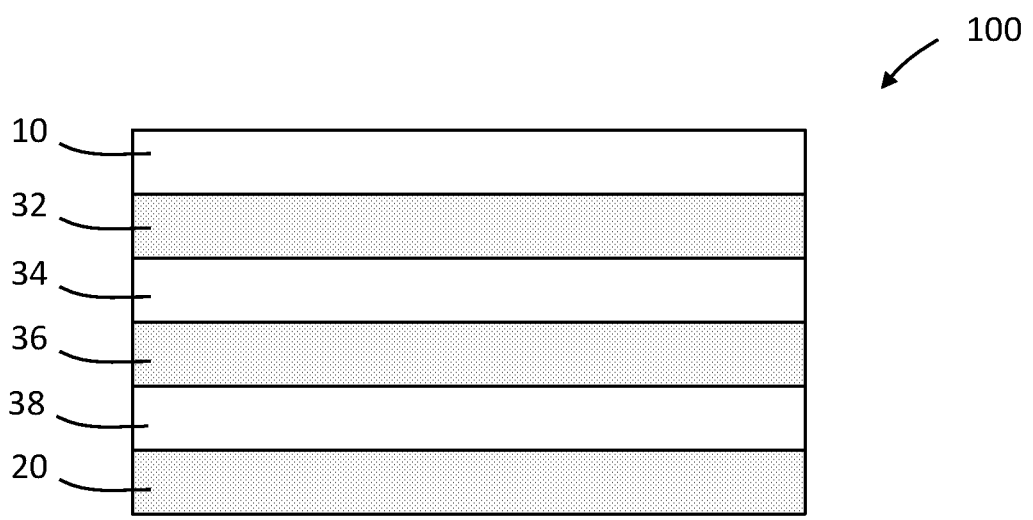
FIGS. 1-3 are schematic sectional views of embodiments of a multilayer packaging films.

DETAILED DESCRIPTION a number to refer to a component in a given figure is not intended to limit the component in another figure labeled with the same number. In addition, the use of different numbers to refer to components is not intended to indicate that the different numbered components cannot be the same or similar to other numbered components.

Reference will now be made in greater detail to various embodiments of the subject matter of the present disclosure, some embodiments of which are illustrated in the accompanying drawings.

The present disclosure describes packaging for produce that provides for controlled, on-demand release of $ClO_2$ gas to disinfect or sterilize produce packaged in the film. The packaging films described herein release $ClO_2$ gas upon exposure to both UV light and moisture. Sufficient moisture may be present in the film or in a package formed from the film, for example due to moisture in the produce disposed in the package, such that the film or package may need only to be exposed to UV light to generate chlorine dioxide under conditions of a manufacturing line on which produce is packaged. Alternatively or in addition, the film may be exposed to an additional source of moisture for generation of chlorine dioxide following or during exposure to UV light.

The packaging is a multilayer packaging film comprising a first layer and a chlorine dioxide-producing layer. The chlorine dioxide-producing layer comprises a polymer composition and a plurality of chlorite ions. The chlorine dioxide-producing layer is substantially free of an energy-activated catalyst and is substantially free of an acid-releasing compound.

As used herein, an "energy-activated catalyst" is a compound that can catalyze the oxidation of $ClO_2^-$ — to $ClO_2$ gas following activation of the catalyst compound by electromagnetic energy, such as visible light. Published U.S. Patent Application 2008/0299066A1 lists a number of compounds and classes of compounds as energy activated catalysts, some of which may be capable of catalyzing the oxidation of $ClO_2^-$ — to $ClO_2$ gas following activation of the catalyst compound by electromagnetic energy. Published U.S. Patent Application 2008/0299066A1 lists metal oxides, metal sulfides, metal chalcogenites, metal phosphides, metal arsenides, non-metal semiconductors, photoactive homopolyanions, photoactive heteropolyanions, and polymeric semiconductors as examples of energy activated catalysts. The chlorine dioxide-producing layers of the films described herein are substantially free of those compounds that can catalyze the oxidation of $ClO_2^-$ — to $ClO_2$ gas following activation of the catalyst compound by electromagnetic energy, particularly visible light.

Published U.S. Patent Application 2008/0299066A1 discloses examples in which titanium dioxide is used as an energy activated catalyst to catalyze the oxidation of $ClO_2^-$ — to $ClO_2$ gas. In some embodiments, the chlorine dioxide-producing layers or the films described herein are substantially free of a metal oxide energy-activated catalyst. In some embodiments, the chlorine dioxide-producing layers or the films described herein are substantially free of titanium dioxide.

As used herein, an "acid-releasing compound" is a compound that, in the presence of moisture, can generate acid and hydronium ions, which hydronium ions can react with chlorite ions to form $ClO_2$ gas. U.S. Pat. No. 6,605,304 lists a number of acid releasing compounds for gas generation including carboxylic acids, esters, anhydrides, acyl halides, phosphoric acid, phosphate esters, trialkylsilyl phosphate esters, dialkyl phosphates, sulfonic acid, sulfonic acid esters, sulfonic acid chlorides, phosphosilicates, phosphosilicic anhydrides, carboxylates of poly α-hydroxy alcohols such as sorbitan monostearate or sorbitol monostearate, phosphosiloxanes, and acid releasing waxes, such as propylene glycol monostearate acid releasing waxes. U.S. Pat. No. 6,605,304 also lists as acid-releasing compounds inorganic acid releasing agents, such as polyphosphates, including tetraalkyl ammonium polyphosphates, monobasic potassium phosphate, potassium polymetaphosphate, sodium metaphosphates, borophosphates, aluminophosphates, silicophosphates, sodium polyphosphates such as sodium tripolyphosphate, potassium tripolyphosphate, sodium-potassium phosphate, and salts containing hydrolyzable metal cations such as zinc. In some embodiments described herein, the chlorine dioxide-producing layers or the films for generating $ClO_2$ gas described herein are substantially-free of such compounds.

In some embodiments, the chlorine dioxide-producing layers or the films described herein are substantially free of an anhydride. In some such embodiments, the chlorine dioxide-producing layer is substantially free of an alcohol, an amide, or an alcohol and an amide.

As used herein, "substantially free of an acid-releasing compound" means that the chlorine dioxide-producing layer includes no acid-releasing compound or includes 2% by weight or less of an acid-releasing compound. In some embodiments, the chlorine dioxide-producing layer includes no acid-releasing compound or includes 1% by weight or less, or 0.5% by weight or less, of an acid-releasing compound. In some embodiments, the ratio (by weight) of acid-releasing compound to chlorite ion source, such as chlorite ion salt, in the chlorine dioxide-producing layer is 1:10 or less. For example, the ratio of acid releasing compound to chlorite ion source may be 1:20 or less, such as 1:50 or less or 1:100 or less.

As used herein, "substantially free of an energy-activated catalyst" means that the chlorine dioxide-producing layer includes no energy-activated catalyst or includes less than 10 weight percent of an energy-activated catalyst based on the total weight of the layer. In some embodiments, the chlorine dioxide-producing layer includes less than 5 weight percent, such as less than 2 weight percent, of an energy-activated catalyst based on the total weight of the layer. In some embodiments, the ratio (by weight) of energy-activated catalyst to chlorite ion source, such as chlorite ion salt, in the chlorine dioxide-producing layer is 1:2 or less. For example, the ratio of energy-activated catalyst to chlorite ion source may be 1:5 or less, such as 1:10 or less or 1:20 or less.

One or more layers of the film, other than the chloride dioxide-producing layer(s), may include greater amounts of one or both of an energy-activated catalyst and an acid-releasing compound than the chloride dioxide-producing layer. One or more of layers of the film, other than the chlorine dioxide-producing layer(s), may also be substantially free of one or both of an energy-activated catalyst and an acid-releasing compound.

Preferably, the multilayer produce packaging films described herein release an amount of chlorine dioxide for a sufficient amount of time to deodorize or disinfect produce packaged within the film.

As used herein, "deodorize" means to remove or conceal an unpleasant smell. In many cases, the unpleasant smell may be caused by odor-causing bacteria, and killing of the bacteria may have a deodorizing effect. A composition described herein may release any suitable amount of $ClO_2$ gas to deodorize a food product, such as produce. For example, a film may release 2 parts per million (ppm) or greater $ClO_2$ into an interior volume defined by a package formed, at least in part, from the film. Typically, a composition may release 10 ppm or greater $ClO_2$ gas to deodorize produce. The concentration of chlorine dioxide may increase over time if the package is sealed, as additional chlorine dioxide is released from the film. The amount of $ClO_2$ gas needed to effectively deodorize produce will depend, in part, on the nature of the produce. In addition, the time that the produce is exposed to $ClO_2$ gas will affect the ability of the $ClO_2$ gas to deodorize the produce. In some embodiments, a composition releases an amount of $ClO_2$ gas for a time sufficient to expose the produce to 2 ppm·hours or greater of $ClO_2$ gas to deodorize the produce. For example, the composition may release 10 ppm·hours or more of $ClO_2$ gas, or 20 ppm·hours or more of $ClO_2$ gas, to deodorize a produce.

As used herein, "disinfect" means to reduce the number of living bacteria. To determine whether produce is disinfected, produce that has undergone a disinfecting treatment, such as exposure to $ClO_2$ gas, can be compared to control produce that has not undergone the disinfecting treatment to determine whether bacterial burden has been reduced; and, if so, the produce will be considered to have been disinfected. Alternatively, the bacterial burden of a produce may be compared before and after treatment to determine whether the produce has been disinfected. A produce packaging film described herein may release any suitable amount of $ClO_2$ gas to disinfect produce disposed within packaging formed from the packaging film. For example, a film may release 10 parts per million (ppm) or greater $ClO_2$ gas into an interior volume defined by a package formed, at least in part, from the film. Typically, the film may release 50 ppm or greater $ClO_2$ gas to disinfect the produce. The amount of $ClO_2$ gas needed to effectively disinfect produce will depend, in part, on the nature of the produce. In addition, the time that the produce is exposed to $ClO_2$ gas will affect the ability of the $ClO_2$ gas to disinfect the produce. In some embodiments, the film releases an amount of $ClO_2$ gas for a time sufficient to expose the produce to 100 ppm·hours or greater of $ClO_2$ gas to disinfect the produce. For example, the film may release 150 ppm·hours or more of $ClO_2$ gas, or 200 ppm·hours or more of $ClO_2$ gas, to disinfect the produce.

Packaging Film

The multilayer produce packaging film comprises a first layer and a chlorine dioxide-producing layer. The chlorine dioxide-producing layer comprises a plurality of chlorite ions and a polymer composition.

In many embodiments, the inner-most layer of the packaging film is the chlorine dioxide-producing layer. In some embodiments, the chlorine dioxide-producing layer is proximate to the inner-most layer of the film and the inner-most layer of the film allows transmission of chlorine dioxide through the inner-most layer. Upon exposure of the chlorine dioxide-producing layer to UV radiation and moisture, $ClO_2$ gas can be released to contact produce in a package produced by the packaging film. The amount of chlorite ion present in the packaging, the time and amount of exposure of the packaging to UV light and the time and amount of moisture to which the packaging is exposed can affect the amount of $ClO_2$ gas generated, and thus can affect the extent to which the produce is deodorized or disinfected.

The packaging film may comprise any suitable number of layers. For example, the packaging film may comprise one or more of a sealing layer, an abuse-resistant outer layer, an intermediate layer, a tie layer, and the like. The film may comprise one or more chlorine dioxide-producing layers.

Chlorine Dioxide-Producing Layer

The chlorine dioxide-producing layer comprises a plurality of chlorite ions and a polymer composition. The chlorite ions may be present in the layer in the form of a salt. The layer may include any suitable chlorite salt. Chlorite salts include both a chlorite anion and a cation. The cation can be an inorganic cation or an organic cation. For example, the cation may be any cation known in the art to be capable of forming a chlorite salt, including, without limitation, an alkali metal ion, and alkaline earth ion, a transition metal ion, a protonated primary amine, a protonated secondary amine, a protonated tertiary amine, a quaternary amine, or mixtures thereof. In some embodiments, the chlorite salt is selected from sodium chlorite and potassium chlorite. The chlorine dioxide-producing layer may include one or more chlorite salts. For example, the chlorine dioxide-producing layer may include sodium chlorite and potassium chlorite.

The chlorine dioxide-producing layer may include any suitable amount of chlorite salt. The amount of chlorite salt can be varied to help control the amount of $ClO_2$ that is generated. In non-limiting examples, the weight percent of the chlorite salt is, for example, 0.1%, 1%, 5%, 10%, 15%, 20%, 25%, 30%, 35%, 40%, 45%, 50%, 55%, 60%, 65% or 70% of the weight of the composition, or any amount in between. In some embodiments, the lower range of the weight of the chlorite salt may be, for example, 0.1%, 1%, 5%, 10%, 15%, 20%, 25%, 30%, 35%, 40%, 45%, 50%, 55%, 60%, or 65% of the weight of the composition, while the upper range of the weight of the chlorite salt may be 15%, 20%, 25%, 30%, 35%, 40%, 45%, 50%, 55%, 60%, 65%, or 70% of the weight of the composition. The disclosure encompasses all weight percentage ranges that are defined by any combination of these lower and upper bounds.

The chlorine dioxide-producing layer may comprise any suitable polymer composition. In some embodiments, the layer comprises one or more of polyethylene, ethylene vinyl acetate, ethylene alpha-olefins, or polypropylene.

The chlorine dioxide-producing layer may be present in any suitable form. For example, the layer may be in the form of a coating layer or a film layer. If the chlorine dioxide-producing layer is in the form of a film layer, the film layer may be co-extruded, laminated or otherwise associated with one or more other layer of the film.

The chlorine dioxide-producing layer may have any suitable thickness. In some embodiments, the layer has a thickness of 25 micrometers or more when the chlorine dioxide-producing layer is in the form of a film layer. A chlorine dioxide-producing film layer may have any suitable amount of chlorite ion in the layer, such as those amounts discussed above. In some embodiments, the chlorine dioxide-producing film layer comprises a chlorite salt in an amount within a range from 0.1 weight percent to 25 weight percent relative to the total weight of the layer. For example, the chlorine dioxide-producing film layer may comprise a chlorite salt in an amount within a range from 5 weight percent to 20 weight percent relative to the total weight of the layer.

In some embodiments, a coating comprising chlorite ions is disposed on a substrate layer to form the chlorine dioxide-producing layer on the substrate layer. The coating may be disposed across an entire surface of the substrate layer or can be disposed across one or more portions of the substrate layer. The coating comprising chlorite ions may be advantageously applied to certain portions of the substrate layer to direct the generation of $ClO_2$ gas (upon exposure to the two-stage gas generation protocol) only to areas where generation of $ClO_2$ gas is desired. Such directed coating and gas generation, can provide cost savings relative to coatings applied across an entire surface, including across areas for which gas generation is not needed or desired.

Any suitable coating composition may be used to coat the substrate layer. For example, the coating composition may comprise one or more chlorite salt, one or more other suitable coating components, and one or more suitable solvents or diluents. In some embodiments, the one or more coating components are water soluble or water dispersible.

Suitable coating components may include materials that retain the chlorite ions on the substrate layer after the article is coated on the substrate layer. In some embodiments, the coating composition comprises a polymer or resin compatible with the substrate layer to be coated. Upon drying or curing of the coating, the coating preferably adheres to the substrate layer.

The coating composition may comprise any suitable polymer. In some embodiments, the coating composition comprises one or more of polyethylene, ethylene vinyl acetate, ethylene alpha-olefins, or polypropylene.

The coating compositions may include any suitable amount of chlorite ion, such as the amounts discussed above. In some embodiments, the chlorite ions are present in a salt, and the salt is present in an amount within a range from 0.1 weight percent to 30 weight percent relative to the total weight of the chlorine dioxide-producing layer. For example, the salt may present in an amount within a range from 10 weight percent to 20 weight percent relative to the total weight of the chlorine dioxide-producing layer The coating composition may be applied in any suitable manner. For example, the substrate layer to be coated may be dipped in the coating composition or the coating composition may be sprayed, rolled, printed, or otherwise deposited on a surface of the substrate layer. In some embodiments, the coating is pattern coated to coat certain portions of a surface of the substrate layer and to leave certain portions of the substrate layer uncoated.

The coating may be applied to have any suitable thickness. In some embodiments, the resulting coating layer has a thickness of about 15 micrometers or less.

Heat Sealing Layers

The films described herein may comprise a heat sealing layer. The terms "heat seal layer" and "sealing layer" are used interchangeably and refer to a layer capable of fusion bonding by conventional indirect heating means which generate sufficient heat on at least one film contact surface for conduction to the contiguous film contact surface and formation of a bond interface therebetween without loss of the film integrity. The bond interface between contiguous inner layers preferably has sufficient physical strength to withstand the packaging process and subsequent handling.

In some embodiments, the heat seal layer comprises a polyolefin. "Polyolefin" is used herein broadly to include polymers such as polyethylene, ethylene-alpha olefin copolymers (EAO), polypropylene, polybutene, ethylene copolymers having a majority amount by weight of ethylene polymerized with a lesser amount of a comonomer such as vinyl acetate, and other polymeric resins falling in the "olefin" family classification. Polyolefins may be made by a variety of processes well known in the art including batch and continuous processes using single, staged or sequential reactors, slurry, solution and fluidized bed processes and one or more catalysts including for example, heterogeneous and homogeneous systems and Ziegler, Phillips, metallocene, single site and constrained geometry catalysts to produce polymers having different combinations of properties. Such polymers may be highly branched or substantially linear and the branching, dispersity and average molecular weight and may vary depending upon the parameters and processes chosen for their manufacture in accordance with the teachings of the polymer arts.

In some embodiments, the heat seal layer comprises a cyclic olefin copolymer (COC), such as an ethylene norbornene copolymer.

In some embodiments, the heat seal layer comprises one or more of polyethylene, ethylene vinyl acetate, ethylene alpha-olefins, or polypropylene.

In some embodiments, the sealing layer comprises a blend of polymers to obtain suitable or desired properties.

In some embodiments, the sealing layer is the chlorine dioxide-producing layer that is capable of generating $ClO_2$ gas upon exposing the film to UV light and moisture. The sealing layer can form the inner-most layer of a package and can thus advantageously place the chlorite ions for generating $ClO_2$ gas in close proximity to an article packaged in the film or to be packaged in the film. The sealing layer may comprise any suitable amount of chlorite ion. However, increasing amounts of chlorite ion, for example in the form of chlorite salt, may interfere with the ability of the layer to seal. Typically, the heat seal layer will comprise less than about 70% by weight chlorite salt, such as 50% or less, 30% or less, 20% or less, or 10% or less. In some embodiments, the heat seal layer comprises a chlorite salt in an amount within a range from 0.1 weight percent to 25 weight percent relative to the total weight of the layer.

If chlorite ions are dispersed in a sealing layer or another layer, the polymer or polymers forming the layer are preferably transparent to UV radiation (e.g., at least 50% of UV light can be transmitted through the polymers forming the sealing layer). However, if the polymer is not particularly transparent to UV light, the intensity of the UV radiation to which the layer is exposed can be increased to expose the chlorite ions to sufficient UV radiation. In addition or alternatively, the thickness of the layer may be decreased to enhance the percentage of the thickness of the layer thorough which sufficient radiation penetrates and/or the concentration of the chlorite ions in the layer can be increased.

In some embodiments, a coating comprising chlorite ions is disposed on the heat seal layer to form the chlorine dioxide-producing layer on the heat seal layer. The coating may be disposed across an entire inner surface of the sealing layer or can be disposed across one or more portions of the sealing layer. For example, the coating may be applied to a portion of the sealing layer that is not involved in heat sealing. Accordingly, the presence of the chlorite ions, for example in the form of chlorite salts, will not adversely affect the heat sealability of the heat seal layer.

Abuse-Resistant Outer Layer

The films described herein may include an outer layer. Since it is seen by the user/consumer, the exterior surface of the film preferably has desirable optical properties and may have high gloss. Also, it preferably withstands contact with sharp objects and provides abrasion resistance, and for these reasons it is often termed the abuse resistant layer. This exterior abuse-resistant layer may or may not also be used as a heat sealable layer and thus may comprise one or more suitable heat seal polymers such as polyethylene or polypropylene. As the exterior surface layer of the film, this layer most often is also the exterior layer of any package, bag, pouch or other container made from the film, and is therefore subject to handling and abuse e.g. from equipment during packaging, and from rubbing against other packages and shipping containers and storage shelves during transport and storage.

The exterior surface layer should be easy to machine (i.e. be easy to feed through and be manipulated by machines e.g. for conveying, packaging, printing or as part of the film or bag manufacturing process). Suitable stiffness, flexibility, flex crack resistance, modulus, tensile strength, coefficient of friction, printability, and optical properties are also frequently designed into exterior layers by suitable choice of materials. This layer may also be chosen to have characteristics suitable for creating desired heat seals which may be resistance to burn through e.g. by impulse sealers or may be used as a heat sealing surface in certain package embodiments e.g. using overlap seals.

Suitable exterior surface layers may comprise: paper, oriented polyester, amorphous polyester, polyamide, polyolefin, cast or oriented nylon, polypropylene, or copolymers, or blends thereof. Oriented films of this or any other layer may be either uni-axially or bi-axially oriented. The exterior layer thickness is typically 0.5 to 2.0 mils. Thinner layers may be less effective for abuse resistance, however thicker layers, though more expensive, may advantageously be used to produce films having unique highly desirable puncture resistance and/or abuse resistance properties.

In some embodiments, the abuse layer is transparent to UV light.

Intermediate Layers

A packaging film described herein may include an intermediate layer. An intermediate layer is any layer between the exterior layer and the interior layer and may include oxygen barrier layers, tie layers or layers having functional attributes useful for the film structure or its intended uses. Intermediate layers may be used to improve, impart or otherwise modify a multitude of characteristics: e.g. printability for trap printed structures, machinability, tensile properties, flexibility, stiffness, modulus, designed delamination, easy opening features, tear properties, strength, elongation, optical, moisture barrier, oxygen or other gas barrier, radiation selection or barrier e.g. to ultraviolet wavelengths, etc. Suitable intermediate layers may include: adhesives, adhesive polymers, paper, oriented polyester, amorphous polyester, polyamide, polyolefin, nylon, polypropylene, or copolymers, or blends thereof. Suitable polyolefins may include: polyethylene, ethylene-alpha olefin copolymers (EAO), polypropylene, polybutene, ethylene copolymers having a majority amount by weight of ethylene polymerized with a lesser amount of a comonomer such as vinyl acetate, and other polymeric resins falling in the "olefin" family classification, LDPE, HDPE, LLDPE, EAO, ionomer, ethylene methacrylic acis (EMA), ethylene acrylic acid (EAA), modified polyolefins e.g. anhydride grafted ethylene polymers, etc.

Tie Layers

A film as described herein may comprise one or more adhesive layers, also known in the art as "tie layers," which can be selected to promote the adherence of adjacent layers to one another in a multilayer film and prevent undesirable delamination. A multifunctional layer is preferably formulated to aid in the adherence of one layer to another layer without the need of using separate adhesives by virtue of the compatibility of the materials in that layer to the first and second layers. In some embodiments, adhesive layers comprise materials found in both the first and second layers. The adhesive layer may suitably be less than 10% and preferably between 2% and 10% of the overall thickness of the multilayer film.

Multilayer films can comprise any suitable number of tie or adhesive layers of any suitable composition. Various adhesive layers are formulated and positioned to provide a desired level of adhesive between specific layers of the film according to the composition of the layers contacted by the tie layers.

The interior, exterior, intermediate or tie layers may be formed of any suitable thermoplastic materials, for example, polyamides, polystyrenes, styrenic copolymers e.g. styrene-butadiene copolymer, polyolefins, and in particular members of the polyethylene family such as LLDPE, VLDPE, HDPE, LDPE, COC, ethylene vinyl ester copolymer or ethylene alkyl acrylate copolymer, polypropylenes, ethylene-propylene copolymers, ionomers, polybutylenes, alpha-olefin polymers, polyesters, polyurethanes, polyacrylamides, anhydride-modified polymers, acrylate-modified polymers, polylactic acid polymers, or various blends of two or more of these materials.

Optional Additives to Layers

Various additives may be included in the polymers utilized in one or more of the exterior, interior and intermediate or tie layers of packaging comprising the same. For example, a layer may be coated with an anti-block powder. Also, conventional anti-oxidants, antiblock additives, polymeric plasticizers, acid, moisture or gas (such as oxygen) scavengers, slip agents, colorants, dyes, pigments, organoleptic agents may be added to one or more film layers of the film or it may be free from such added ingredients.

Reflective Layers

The packaging films may include one of more layers that reflect UV light. Examples of suitable materials for such layers include metallic oils or depositions like vacuum metallized or sputtered layers. The reflective layer could be applied as a coating where reflective particles such as metallic flakes are dispersed in a polymeric binder. The film may be configured such that the chlorine dioxide-producing layer is positioned between the reflective layer and the UV source when the film is exposed to UV radiation. In some such embodiments, the one or more reflective layer(s) is/are in contact with the polymeric film. The reflective layers may be optically engineered to maximize yield, by increasing UV exposure of the chlorite salts dispersed within the film (e.g., dispersed within a sealing layer or a coating disposed on the sealing layer).

In cases where the polymers or additives of one or more layers of the film are not transparent to UV light (e.g., block transmission of more than 50% of UV light) or reflect UV light, care may need to be taken to ensure that the chlorine dioxide-producing layer (e.g., seal layer or coating disposed on seal layer) can be exposed to sufficient amounts of UV radiation to generate $ClO_2$ gas. In some embodiments, a packaging film is subjected to UV radiation prior to final sealing of the packaging to ensure that the chlorine dioxide-producing layer is subjected to sufficient UV radiation to generate $ClO_2$ gas upon subjecting the film to a two-stage gas generation protocol. For example, the packaging manufacturing line can be equipped with an appropriate UV emitting source to allow in-line UV irradiation of the chlorine dioxide-producing layer.

Oxygen Transmission of the Films

A multilayer film for packaging produce described herein preferably has an oxygen transmission rate that allows for suitable exchange of air across the film to maintain freshness of the produce packaged in the film. The packaging films may have any suitable oxygen transmission rate. For example, the film may have an oxygen transmission rate of at least 775 $cm^3/m^2/24$ hours (50 $cm^3/100$ $in^2/24$ hours), such as an oxygen transmission rate of at least 3100 cm$^3$/m$^2$/24 hours (200 cm$^3$/100 in$^2$/24 hours). One of skill in the art of packaging manufacturing will understand that the selection of materials and layers for the multilayer packaging film will affect the oxygen transmission rate of the film and will be readily able to select appropriate materials and layers to achieve a suitable oxygen transmission rate for packaging produce.

Examples of polymers that can be used to achieve high oxygen transmission rates include polyethylene, polypropylene such as oriented polypropylene, styrene polymers such as styrene-butadiene copolymers, polymethylpentene, cyclic olefin copolymers (COC), and the like. It will be understood that the thickness of the films and layers will affect the oxygen transmission rates, with thinner films and layers tending to allow for greater oxygen transmission.

Materials and layers that have low oxygen transmission rates or that are considered oxygen barriers can also be used if one or more openings are created through the packaging to allow exchange of air across the film through the openings.

Methods of Manufacture

The packaging films described herein may be made in any suitable manner, such as by conventional processes. Processes to produce flexible films may include e.g. cast or blown film processes, or extruding processes.

Packages may be formed from films in any suitable manner. In some embodiments, the packages are formed by heat sealing a film to itself or another suitable film. In some embodiments, packages such as pouches are thermoformed. In some embodiments, films are heat sealed across an opening of a container.

Film Thickness

A packaging film described herein may have any suitable thickness. In some embodiments, the packaging film has a total thickness of less than about 50 mils, more preferably the film has a total thickness of from about 1.0 to 10 mils (25-250 microns ($\mu$), such as from about 1 to 5 mils, or from about 2 to 3.5 mils. For example, entire multilayer films or any single layer of a multilayer film can have any suitable thicknesses, including 1, 2, 3, 4, 5, 6, 7, 8, 9, 10, or 50 mils, or any increment of 0.1 or 0.01 mil therebetween.

In some embodiments, the packaging films are as thick as 50 mils (1270 microns) or higher, or as thin as 1 mil (25.4 microns) or less. In various embodiments, the packaging films have a thickness of between about 2-4 mil (51-102 microns).

Tearing Aid or Tear Initiator

The packaged articles that include an article disposed within sealed packaging may include a tearing aid or tear initiator such as a notch. Examples of tearing aids or tear initiators include notches, slits, perforations, surface roughened portions, etc. Such tear initiators may be used on one or more edges of a package such as a pouch.

Advantageously the tear initiator may be used with scoring e.g. mechanical or laser scoring of one or more layers, preferably the other abuse resistance layer, to create a tear directing line which facilitates opening.

Examples of Embodiments of Multilayer Films

In some embodiments, a multilayer produce film comprises a first layer, and a chlorine dioxide-producing layer. The chlorine dioxide-producing layer comprises a polymer composition and a plurality of chlorite ions. The chlorine dioxide-producing layer is substantially free of an energy-activated catalyst and is substantially free of an acid-releasing compound. In some embodiments, the plurality of chlorite ions are present in a salt selected from the group consisting of sodium chlorite, potassium chlorite, and mixtures thereof. In some embodiments, the film has an oxygen transmission rate of at least 775 cm$^3$/m$^2$/24 hours (50 cm$^3$/100 in$^2$/24 hours), such as an oxygen transmission rate of at least 3100 cm$^3$/m$^2$/24 hours (200 cm$^3$/100 in$^2$/24 hours). In some embodiments, the first layer is an abuse-resistant layer, wherein the abuse-resistant layer is UV-light transparent.

In some embodiments, the chlorine-dioxide-producing layer is a coating having a thickness less than 15 µm. In some embodiments, the coating comprises at least one of polyethylene, ethylene vinyl acetate, ethylene alpha-olefins, or polypropylene. In some embodiments, the coating comprises a chlorite salt in an amount within a range from 0.1 weight percent to 20 weight percent relative to the total weight of the chlorine dioxide-producing layer. For example, the coating comprises a chlorite salt in an amount within a range from 1 weight percent to 15 weight percent relative to the total weight of the chlorine dioxide-producing layer.

In some embodiments, the chlorine dioxide-producing layer may be a film layer and has a thickness of at least 25 µm. In such embodiments, the polymer composition may comprise at least one of polyethylene, ethylene vinyl acetate, ethylene alpha-olefins, or polypropylene. The plurality of chlorite ions may be present in a salt, and the salt may be present in an amount within a range from 0.1 weight percent to 20 weight percent relative to the total weight of the chlorine dioxide-producing layer, such as within a range from 1 weight percent to 15 weight percent relative to the total weight of the chlorine dioxide-producing layer.

In some embodiments, the multilayer produce film has a layer composition in the following sequence: (i) the chlorine dioxide-producing layer; (ii) a layer of polyethylene; (iii) a layer of adhesive; and (iv) the first layer comprising oriented polypropylene. The film may also have optional additional layers dispersed within the sequence.

In some embodiments, the multilayer produce film has a layer composition in the following sequence: (i) the chlorine dioxide-producing layer; (ii) the first layer comprising oriented polypropylene; (iii) a layer of adhesive; and (iv) a second layer of oriented polypropylene. The film may also have optional additional layers dispersed within the sequence.

In some embodiments, a produce package comprises a sidewall comprising the multilayer produce film. The produce package comprises an interior volume defined, at least in part, by an inside surface of the sidewall. In some embodiments, the chlorine dioxide-producing layer is proximate the inside surface of the sidewall. In some embodiments, the sidewall comprises a heat seal of the chlorine dioxide-producing layer.

Referring now to FIG. 1, a multilayer produce film 100 is shown. The film 100 includes a first layer 10, which may be an outer layer (as depicted) but can be an inner layer or an intermediate layer. The film 100 also includes a chlorine dioxide-producing layer 20 that contains a polymer composition and chlorite ions. The chlorine dioxide-producing layer 20 can be a film layer or a coating layer. The depicted film 100 includes optional intervening layers 32, 34, 36, and 38.

Figure 2:
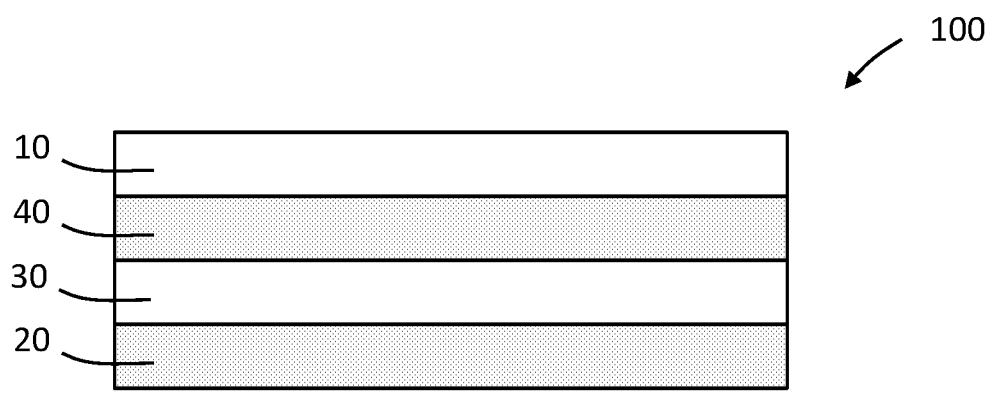

Referring now to FIG. 2, a multilayer produce packaging film 100 is shown. The film 100 includes in the following sequence: the chlorine dioxide-producing layer 20; a layer of polyethylene 30; a layer of adhesive 40; the first layer 10 comprising an oriented polypropylene. The film 100 may comprise optional intervening layers (not shown).

Figure 3:
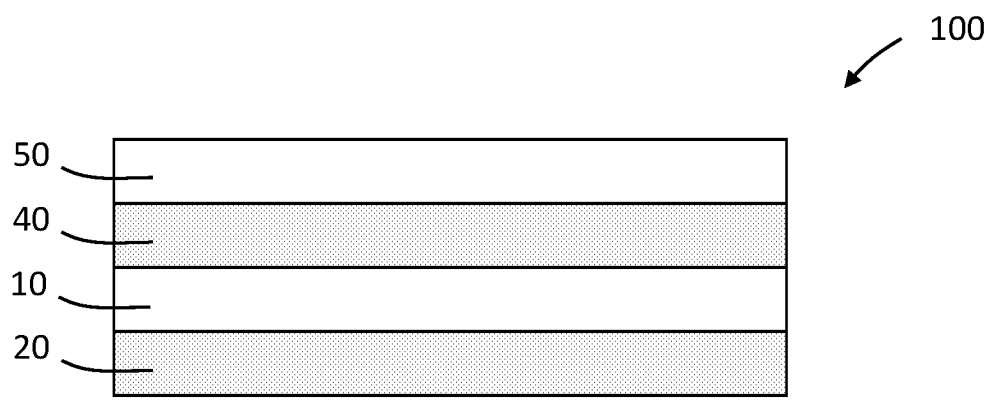

Referring now to FIG. 3, a multilayer produce packaging film 100 is shown. The film 100 includes in the following sequence: the chlorine dioxide-producing layer 20; the first layer 10 comprising an oriented polypropylene; a layer of adhesive 40; a second layer comprising an oriented polypropylene 50. The film 100 may comprise optional intervening layers (not shown).

Figure 4:
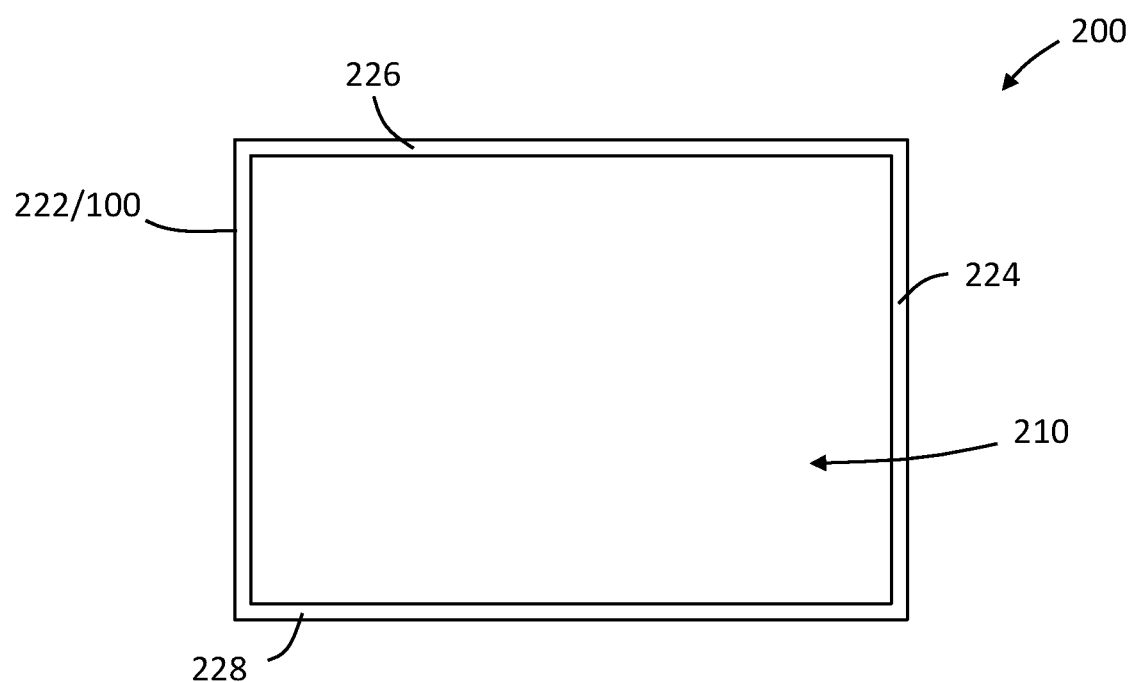
FIG. 4 is a schematic sectional view of an embodiment of a medical package.

Referring now to FIG. 4, a produce package 200 is shown. The depicted package 200 includes first 222, second 224, third 226, and fourth 228 sidewalls that at least partially define an interior volume 210 of the package. The first sidewall 222 comprises a multilayer packaging film 100 comprising a chlorine dioxide-producing layer. The other sidewalls 224, 226, 228 may or may not include a multilayer packaging film having a chlorine dioxide-producing layer. In some embodiments, all of the side walls comprise a multilayer packaging film comprising a chlorine dioxide-producing layer.

Packaged Products

Any suitable produce may be disposed in a package comprising the multilayer packaging film described herein. For example, lettuce, grapes, spinach, or the like may be disposed within a sealed package as described herein. Preferably, the packaging generates a sufficient amount of $ClO_2$ gas for a sufficient amount of time after being exposed to UV light and moisture to disinfect the produce.

Gas Generation

The films, packages or packaged produce described herein may be exposed to UV radiation and moisture in any suitable manner to generate chlorine dioxide from the chlorine dioxide-producing layer(s). The films may be exposed first to moisture and then to UV light, first to UV light and then moisture, or simultaneously exposed to UV light and moisture to release $ClO_2$. Sufficient moisture may be present in the film or in a package formed from the film, for example due to the produce disposed in the package, such that the film or package need only be exposed to UV light to produce $ClO_2$.

In some embodiments, the films, packages or packaged produce are first exposed to UV light and then later exposed to moisture to generate chlorine dioxide. The films, packages or packaged produce that have previously been exposed to UV light may be exposed to any suitable source of moisture to generate chlorine dioxide. For example, the films, packages, or packaged produce may be exposed to water vapor or humidified gas.

The amount of $ClO_2$ generated from a film as described herein can be regulated by, for example, varying the wavelength and exposure time of the ultraviolet light, the amount of water vapor (moisture) present, the concentration of chlorite salts in the composition, or the length of the storage period.

In some embodiments, the UV light has a wavelength in the range of about 200 nm to 400 nm. In some such embodiments, the UV light has a wavelength in the range of about 230 nm to 320 nm. In some such embodiments, the UV light has a wavelength in the range of about 240 nm to 280 nm. Preferably, the UV light includes light having a wavelength of 254 nm.

In some embodiments, the packaged produce, package or film is exposed to UV light for a period of time that is greater than 10 milliseconds. In some such embodiments, the packaged produce, package, or film is exposed to UV light for a period of time that is greater than 10 seconds. In some embodiments, the packaged produce, package or film is exposed to UV light for a period of time that is greater than ten minutes.

In some embodiments, the step of exposing the packaged produce, package or film to ultraviolet light may be repeated one or more times, as can the step of subsequently contacting the packaged produce, package or film with moisture to generate $ClO_2$ gas.

In some embodiments, packaged produce, package or film is exposed to humidified gas. The humidified gas may have any suitable relative humidity. For example, the relative humidity of the humidified gas may be within the range of about 1% to 100%. In some such embodiments, the relative humidity of the humidified gas is within the range of about 20% to 100%. In some such embodiments, the relative humidity of the humidified gas is within the range of about 60% to 100%. In some such embodiments, the relative humidity of the humidified gas is within the range of about 75% to 100%.

In some embodiments, the steps of (a) exposing the packaged produce, package or film including a chlorine dioxide-producing layer to UV light, and (b) subsequently contacting the packaged produce, package or film with moisture, are separated by an intervening storage time. In some such embodiments, the intervening storage time is within the range of about one minute to about two days. In some such embodiments, the storage time is within the range of about one hour to about one day.

In some embodiments, a method for generating $ClO_2$ gas includes the steps of (a) exposing a packaged produce, package or film including a chlorine dioxide-producing layer to ultraviolet (UV) light, and (b) subsequently exposing the packaged produce, package or film to moisture, whereby $ClO_2$ gas is generated. Alternatively, the method includes the steps of (a) exposing a packaged produce, package or film including a chlorine dioxide-producing layer to moisture, and (b) subsequently exposing the packaged produce, package or film to ultraviolet (UV) light. Optionally, these steps may be repeated one or more times to generate additional amounts of $ClO_2$ gas.

In some embodiments, the step of exposing the film to moisture comprises contacting the film with the produce.

As used herein and in the appended claims, the singular forms "a," "an," and "the" include plural reference unless the context clearly dictates otherwise. As well, the terms "a" (or "an"), "one or more" and "at least one" can be used interchangeably herein. The terms "comprising," "including," and "having" can be used interchangeably.

Unless defined otherwise, all technical and scientific terms used herein have the same meanings as commonly understood by one of ordinary skill in the art to which this invention belongs. All publications and patents specifically mentioned herein are incorporated by reference for all purposes.

The following examples are offered for illustrative purposes only, and is not intended to limit the scope of the present invention in any way. Indeed, various modifications of the invention in addition to those shown and described herein will become apparent to those skilled in the art from the foregoing description and the following examples and fall within the scope of the appended claims.

EXAMPLES

Varying Amounts of Energy-Activated Catalyst

Equal parts of titanium dioxide (99.1% TiO2; Sigma-Aldrich, St. Louis, Mo.) and sodium chlorite (technical grade; 80% NaClO2; Sigma-Aldrich, St. Louis, Mo.) were mixed and suspended in water, and subsequently left in an open container until most of the water evaporated. The samples were evaporated (but not dried) in complete darkness, without exposure to visible or UV light sources. Similar blends were made with 2:1, 10:1, 20:1, and 65:1 sodium chlorite to titanium dioxide ratios. For testing, individual samples of the blends were placed in small glass vials of volume 20 mL and hermetically sealed. After sealing, the vials were exposed to a compact fluorescent light source for approximately 4.5 hours. A $ClO_2$ detector (PortaSens II, Analytical Technology Inc., Collegeville, Pa.) was used to measure the concentration of the gas generated (see results in Table 1). Subsequently, the samples were exposed to a UV light source (254 nm, Spectrolinker) for 15 seconds. Again, the concentration of $ClO_2$ in the vials was measured and is reported in Table 1.

TABLE 1

Concentration of $ClO_2$ after fluorescent light and UV light exposure. The upper detection limit of the sensor was 240 ppm.

| Sample Reference | Sample mass (g) | $NaClO_2$ to $TiO_2$ to weight ratio | $ClO_2$ concentration after fluorescent light exposure | $ClO_2$ concentration after UV (254 nm) light exposure |
|---|---|---|---|---|
| Sample 1 | 2.31 | 1:1 | >240 ppm | >240 ppm |
| Sample 2 | 1.83 | 2:1 | >240 ppm | >240 ppm |
| Sample 3 | 1.55 | 10:1 | 171 ppm | >240 ppm |
| Sample 4 | 1.50 | 20:1 | 196 ppm | >240 ppm |
| Sample 5 | 1.46 | 65:1 | 151 ppm | >240 ppm |
| Sample 6 | 1.39 | $NaClO_2$ only | 63 ppm | >240 ppm |

Produce Packaging Example 1

A two layer cast film was extruded which consisted of an EVOH layer and a polyethylene layer containing 16% of the sodium chlorite additive. Pouches were made using this film (19 cm length, 19 cm width) with the PE layer as the interior food contact layer. The pouches were exposed to 80% RH at 35° C. for approximately 12 hours. After conditioning, the pouches were filled with 20 g baby spinach and sealed. Additional testing was done with empty pouches. The pouches were exposed to 254 nm UV for 3 s or 5 s (one side only). The concentration of chlorine dioxide generated in the pouches was recorded using a PortaSens II gas leak detector. The concentration measurement was taken approximately 1 minute after UV exposure. The results are shown in Table 2. The lower $ClO_2$ readings for the pouches that contained spinach is theoretically due to degradation of the $ClO_2$ as it is reduced by the pouch contents.

TABLE 2

Concentration of $ClO_2$ in a sealed pouch with and without spinach.

| | ppm $ClO_2$ | |
|---|---|---|
| UV Exposure time (254 nm) | No Spinach | With Spinach |
| 3 seconds | 45.55 | 11.6 |
| 5 seconds | 67.25 | 16.65 |

Produce Packaging Example 2

To verify its efficacy against pathogenic bacteria, pouch samples were sent to Institute of Food Safety and Health (IFSH) for a microbial study where they were filled with 30 grams of lettuce that was inoculated with the *L. monocytogenes* with an initial count of 7.6E+06 CFU/g. The pouches were the same structure and size as Produce Packaging Example 1. The pouches were exposed to 3 s or 5 s of 254 nm UV radiation and analyzed for the microbial kill at 1 and 5 days. It should be noted that the control sample did not contain any $ClO_2$ additive (LDPE sealant laminated to OPP). The pouches containing the ClO2 additive were either pre humidified to 80% RH or left unconditioned. The moisture required for the chlorine dioxide production in the dry samples came from the lettuce. It was observed that chlorine dioxide was able to attain 4-5 log kill in 5 days post inoculation and packaging. The results are summarized in Table 3.

TABLE 3

Log count of *L. monocytogenes* inoculated lettuce

| | | Log Count | | |
|---|---|---|---|---|
| Test Time, post packaging | Conditioning environment | No $ClO_2$ Additive | $ClO_2$ Additive, 3 seconds UV exposure | $ClO_2$ Additive, 5 seconds UV exposure |
| 1 day | Ambient | 6.88 | 4.39 | 5.56 |
| 1 day | 80% RH | 6.88 | 4.63 | 3.54 |
| 5 days | Ambient | 6.74 | 2.4 | 2.38 |
| 5 days | 80% RH | 6.74 | 1 | 1.48 |

All publications and patents specifically mentioned herein are incorporated by reference for all purposes. Those skilled in the art will recognize, or be able to ascertain using no more than routine experimentation, numerous equivalents to the specific materials and methods described herein. Such equivalents are considered to be within the scope of this invention and encompassed by the following claims.

We claim:

1. A multilayer produce packaging film comprising:
a first layer, and
a chlorine dioxide-producing layer comprising a polymer composition and a source of chlorite ions;
wherein the chlorine dioxide-producing layer comprises:
(i) less than 2% by weight of an energy-activated catalyst, (ii) a ratio of the energy-activated catalyst to the source of chlorite ions of 1:20 or less, (iii) and no acid-releasing compound.

2. The multilayer produce packaging film according to claim 1, wherein the source of chlorite ions is a salt selected from the group consisting of sodium chlorite, potassium chlorite, and mixtures thereof.

3. The multilayer produce packaging film according to claim 1, wherein the film has an oxygen transmission rate of at least 775 cm$^3$/m$^2$/24 hours (50 cm$^3$/100 in$^2$/24 hours).

4. The multilayer produce packaging film according to claim 1, wherein the film has an oxygen transmission rate of at least 3100 cm$^3$/m$^2$/24 hours (200 cm$^3$/100 in$^2$/24 hours).

5. The multilayer produce packaging film according to claim 1, wherein the chlorine-dioxide-producing layer is a coating having a thickness less than 15 μm.

6. The multilayer produce packaging film according to claim 5, wherein the polymer composition comprises at least one of polyethylene, ethylene vinyl acetate, ethylene alpha-olefins, or polypropylene.

7. The multilayer produce packaging film according to claim 5, wherein the source of chlorite ions comprises a salt, wherein the salt is present in an amount within a range from 0.1 weight percent to 20 weight percent relative to the total weight of the chlorine dioxide-producing layer.

8. The multilayer produce packaging film according to claim 5, wherein the source of chlorite ions comprises a salt, wherein the salt is present in an amount within a range from 1 weight percent to 15 weight percent relative to the total weight of the chlorine dioxide-producing layer.

9. The multilayer produce packaging film according to claim 1, wherein the chlorine-dioxide layer has a thickness of at least 25 μm.

10. The multilayer produce packaging film according to claim 9, wherein the polymer composition comprises at least one of polyethylene, ethylene vinyl acetate, ethylene alpha-olefins, or polypropylene.

11. The multilayer produce packaging film according to claim 9, wherein the source of chlorite ions comprises a salt, wherein the salt is present in an amount within a range from 0.1 weight percent to 20 weight percent relative to the total weight of the chlorine dioxide-producing layer.

12. The multilayer produce packaging film according to claim 9, wherein the source of chlorite ions comprises a salt, wherein the salt is present in an amount within a range from 1 weight percent to 15 weight percent relative to the total weight of the chlorine dioxide-producing layer.

13. The multilayer produce packaging film according to claim 1, wherein the first layer is an abuse-resistant layer, wherein the abuse-resistant layer is UV-light transparent.

14. The multilayer produce packaging film according to claim 1, wherein the film has a layer composition in the following sequence:
   the chlorine dioxide-producing layer;
   a layer of polyethylene;
   a layer of adhesive; and
   the first layer comprising an oriented polypropylene,
   wherein optional additional layers may be dispersed within said sequence.

15. The multilayer produce packaging film according to claim 1, wherein the film has a layer composition in the following sequence:
   the chlorine dioxide-producing layer;
   the first layer comprising an oriented polypropylene;
   a layer of adhesive; and
   a second layer of oriented polypropylene;
   wherein optional additional layers may be dispersed within said sequence.

16. A produce package comprising a sidewall comprising the multilayer produce packaging film according to claim 1, wherein the produce package comprises an interior volume defined by an inside surface of the sidewall.

17. The produce package according to claim 16, wherein the chlorine dioxide-producing layer is proximate the inside surface of the sidewall.

18. The produce package according to claim 16, wherein the sidewall comprises a heat seal of the chlorine dioxide-producing layer.

19. A multilayer produce packaging film comprising:
   a first layer, and
   a chlorine dioxide-producing layer comprising a polymer composition and a source of chlorite ions;
   wherein the chlorine dioxide-producing layer comprises:
      no energy-activated catalyst; and no acid-releasing compound.

* * * * *